United States Patent [19]

Brown

[11] 4,191,291

[45] Mar. 4, 1980

[54] DENTAL ORGANIZER AND CONTAINER

[76] Inventor: Ronald W. Brown, 8060 Montgomery Rd., Cincinnati, Ohio 45236

[21] Appl. No.: 6,931

[22] Filed: Jan. 25, 1979

[51] Int. Cl.$^2$ ............................ B65D 1/36; B65D 85/00
[52] U.S. Cl. .................................... 206/369; 206/379; 206/561; 206/562; 206/565; 422/297
[58] Field of Search ...................... 206/63.5, 207, 210, 206/363, 368–370, 372–373, 379, 526, 557–558, 561–564; 211/60 T, 69; 220/20; 312/209; 422/297, 300

[56] References Cited

U.S. PATENT DOCUMENTS

| D. 221,035 | 6/1971 | Raines | 206/561 X |
|---|---|---|---|
| 1,116,310 | 11/1914 | Maser | 206/562 X |
| 1,451,806 | 4/1923 | Baldridge et al. | 206/369 |
| 2,971,637 | 2/1961 | Simons | 206/369 |
| 3,305,124 | 2/1967 | Whiteford | 206/564 |
| 3,467,247 | 9/1969 | Weiss | 206/561 |
| 3,532,221 | 10/1970 | Kaluhiokalani | 206/564 X |
| 3,670,938 | 6/1972 | Brocato | 206/564 X |

FOREIGN PATENT DOCUMENTS

| 60650 | 4/1912 | Fed. Rep. of Germany | 206/369 |
|---|---|---|---|
| 1475924 | 2/1967 | France | 206/558 |

*Primary Examiner*—Steven E. Lipman
*Attorney, Agent, or Firm*—Sughrue, Rothwell, Mion, Zinn and Macpeak

[57] ABSTRACT

A hollow dental tool holder block formed of a thermoplastic base including small diameter holes at spaced positions to receive inserted ends of rod-like dental burs, endodontic files or the like. The block bears a rectangular recess to one side holding a removable, partitioned, open-top tray nested to the block recess. The tray holds paper, cotton products and may be removed from the block when the metal tools borne by the block are submerged within a cleaning solution and treated to ultrasonic vibration, and then reinserted in order to sterilize the entire set of instruments and cotton-paper products.

1 Claim, 4 Drawing Figures

DENTAL ORGANIZER AND CONTAINER

FIELD OF THE INVENTION

This invention relates to dental tool holders, and more particularly, to a highly versatile dental tool holder which holds metal tools and paper, cotton balls and the like.

BACKGROUND OF THE INVENTION

Dental tool holders formed of a generally plan perforated sheet which receive the inserted ends of a metal dental hook burs, files, etc., permit the dentist to readily remove a desired file, bur, or like grinding tool, and return the same after use. U.S. Pat. No. 1,451,806 to Baldridge discloses such a structure. Further, sterilizable instrument and appliance containers have been employed in the form of double-walled molded plastic rectangular trays to support metal tools for surgery and the like. The tray and the tools carried thereby is submerged within a body of liquid where, the tools are subjected to ultrasonic vibrations for cleaning of the same in the presence of cleaning solution. Alternatively, the instrument container may be placed in a steam and subjected to a temperature in excess of 120° C. for sterilization of the surgical tools and the like. Trays or containers of this nature are the subject of U.S. Pat. No. 3,437,423 to Mondiadis.

In the dental field, the dentist requires, at his hand, not only the burs and files constituting grinding tools, but various clamps, cotton balls or pellets, absorbent paper points, and the like. Where the block supporting the files and burs is required to be placed within a solution for ultrasonic cleaning of the tools and subsequently within a high-temperature oven for sterilization, it is impossible to permit that block to retain cotton pellets, paper products, and the like, since they would be ruined by submersion within the cleaning liquid.

SUMMARY OF THE INVENTION

The present invention comprises an improved dental tool holder block comprising a thermoplastic molded base defining a hollow tool holding a structure. Small diameter holes are provided (within the block) at spaced positions to receive the inserted ends of rod-like dental burs, files, or the like. The block bears preferably a rectangular recess within the same and a removable, open-top partitioned thermoplastic material tray having sidewalls corresponding in size and configuration to the block recess is nested within the recess. The files and burs carried within the block small-diameter holes may be subject to ultrasonic cleaning and sterilization subsequent to the removal of the tray bearing the paper products and cotton pellets with the tray returnable subsequent to cleaning and before sterilization to permit the dentist to have ready access to the block carried cotton or paper elements and the cleaned sterilized metal tool bits.

Preferably, the thermoplastic molded block comprises integral, raised cylindrical posts for support of rubber-dam clamps to the side of the small diameter holes supporting the dental burs, endodontic files, etc. The removable tray preferably comprises intersecting vertical transverse and longitudinal partitions and an integral, lift pin at the intersection of said partitions which extends upward above the open top of the tray to permit ready grasping of the tray and removal of the tray from the block.

DESCRIPTION OF THE PREFERRED EMBODIMENT

Figure 1:
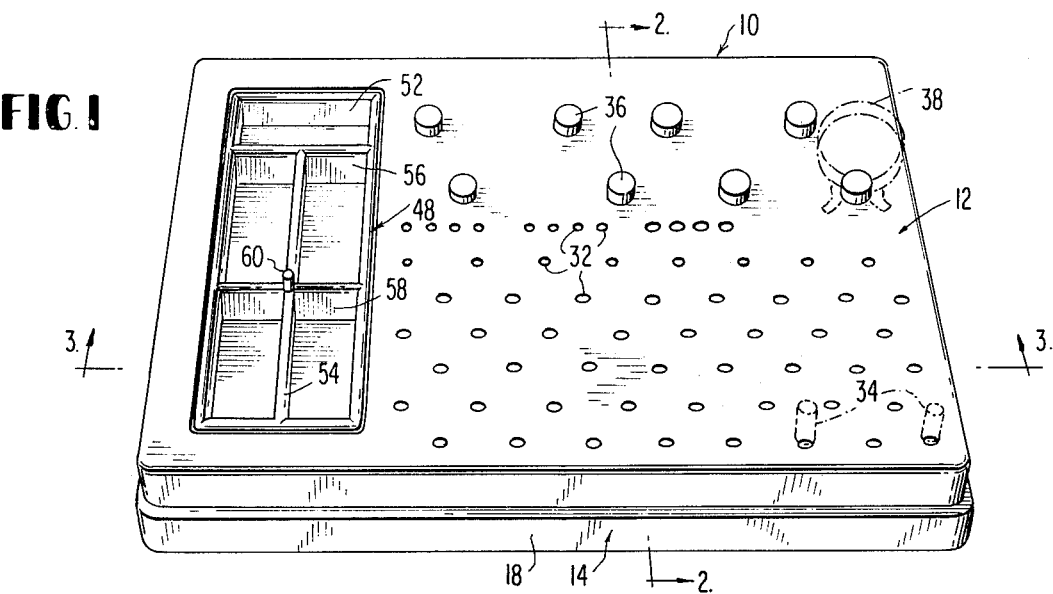
FIG. 1 is a front and top perspective view of the improved endodontic instrument block of the present invention.
Figure 2:
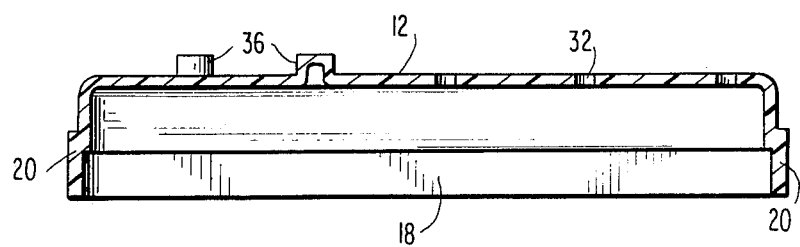
FIG. 2 is a vertical, sectional view of the block of FIG. 1 taken about line 2—2.

Turning to the figures, the dental tool holder or endodontic instrument block indicated generally at 10 is preferably formed of thermoplastic material such as nylon or the like, molded by suitable plastic molding technique, in form of two connected components. A top 12 is integrally molded with base 14. The components are generally rectangular in shape with the base including integral sidewalls 18, extending longitudinally from end to end and merging into opposed end walls 20. The base is therefore open at the bottom. The top 12 and the base 14, therefore, define a hollow-molded block 10. The block top is provided with a multiple row of drilled holes of various diameters as at 32, in given rows, to permit the butt ends of files, burs and the like to be inserted therein, the files being shown in dotted fashion at 34, FIG. 1. The holes 32 cover only a limited surface area. Additionally, there are provided integrally molded projections which are circular in form constituting posts 36 which function to support rubber-dam clamps as indicated in dotted lines at 38, FIG. 1. The clamps are essentially of ring form and are supported and oriented vertically in the plane of the post whose outer surface is gripped thereby.

Figure 4:
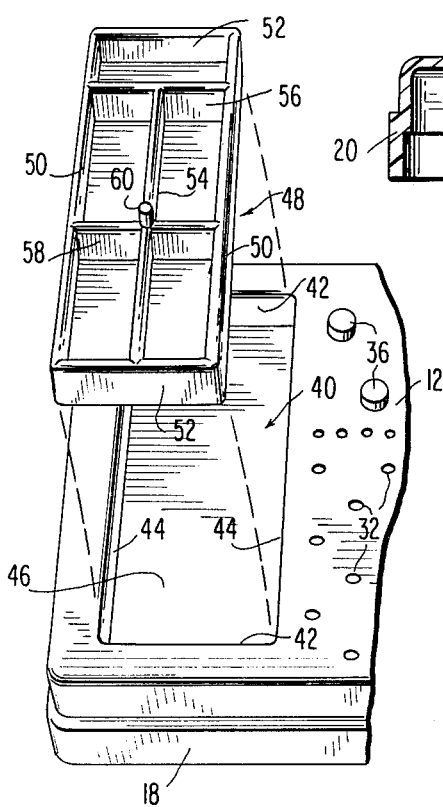
FIG. 4 is an exploded perspective of a portion of the block of FIG. 1, with the removable tray lifted from the recess within the block.
Figure 3:
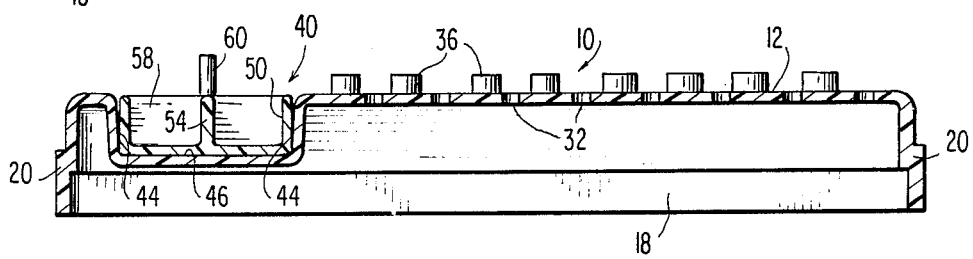
FIG. 3 is a vertical sectional view of the block of FIG. 1 taken about line 3—3.

The top 12 is characterized by a surface recess of rectangular configuration indicated generally at 40, to the left in FIGS. 1, 3 and 4. The recess 40 is defined by opposed end-walls as at 42, laterally opposed sidewalls as at 44, and a recessed bottom wall 46. The vertical height of the recess 40 is somewhat less than the vertical height of the block 10. A removable rectangular tray indicated generally at 48 and formed of molded plastic identical to that forming the top 12 and base 14 is sized and configured to recess 40 so as to be nested or received therein with its upper edge flush with the surface of the top 12 bearing the recess 40. In that respect, the removable tray is provided with laterally opposed longitudinally extending sidewalls as at 50, intersecting transverse end walls 52, and is provided with a central longitudinal partition 54 which does not extend the complete length of the tray but stops short at one end to intersect a first transverse partition 56. At approximately the center, a second transverse partition 58 intersects the longitudinal partition 54 and at this point of intersection, there is provided an integral, molded, cylindrical lift pin as at 60 which projects upwardly above the surface of the top 12, such that the tray can be removed by grasping the lift pin 60 and pulling upwardly. The tray 48 is completed by an integral bottom wall 62 with the top of the tray 48 being open. The tray functions to receive various paper products such as cotton pellets, absorbent paper points, and the like necessary to the normal needs of dental operation.

Unique to the present invention is the concept which permits all of the metal instruments such as the dental burs, files, borne within the holes 32 as well as the rubber-dam clamp and the like as at 38 to be borne by instrument block 10 with the tray 48 removed prior to submergence of the block and its tools within a cleaning liquid for ultrasonic cleaning of the tool bits. Subsequently, the clean instruments and removable tray with paper products may be placed in a suitable oven or the like for high-temperature sterilization. After the block is taken out of the cleaning solution, the removable tray with the paper products contained therein is *reinserted* into the block for sterilization. The removable tray 48, placed back within recess 40 in the endodontic instrument block, is fully stocked to permit the dentist's ready access to needed equipment during patient handling and access to materials needed during normal dental operations such as root canal therapy, filling, etc.

While the invention has been particularly shown and described with reference to a preferred embodiment thereof, it will be understood by those skilled in the art that the foregoing and other changes in form and details may be made therein without departing from the spirit and scope of the invention.

What is claimed is:

1. An improved multi-part plastic dental tool and equipment holder for joint and separate treatment of metallic dental burs, files, etc., having rod-like ends, and rubber dam clamps, and cotton pellets, paper points, and the like, the holder comprising:
   a hollow tool-holding block having a top, side walls and end walls, the top having an upper surface;
   the top having a plurality of small diameter holes formed therein at spaced positions and receiving the rod-like ends of the burs, files, etc., the holes being arranged in rows;
   a series of integrally molded vertically projecting, cylindrical posts extending upwardly from the top of the block, and spaced from said holes, the posts supporting the vertically oriented rubber dam clamps in frictional grip therewith;
   the block having a recess formed therein adjacent one end wall thereof and spaced from the holes and the posts, the recess being defined by end walls and side walls and having a bottom wall;
   a removeable, open top partitioned tray of said thermoplastic material having a series of walls with upper edges corresponding in depth to the walls of the recess and having a bottom which seats on the bottom wall of the recess;
   the tray having its wall upper edges coplaner with the upper surface of the top of the block;
   the tray including a longitudinally extending vertical partition and at least one intersecting transverse partition, and an integral lift pin projecting upwardly at the intersection of said partition such that the pin is readily grasped for removal of the tray from the recess;
   the tray being vertically removeable with its contents whereby, upon removal of the tray, the block with the metallic dental burs, files, etc., and the rubber dam clamps is submerged in a cleaning solution for cleaning thereof; and
   said tray being reinserted whereby said holder and said tray are placed in a dry-heat oven or the like for high temperature sterilization of the contents.

* * * * *